(12) United States Patent
Klein et al.

(10) Patent No.: US 6,500,830 B1
(45) Date of Patent: Dec. 31, 2002

(54) CONVERSION OF MODIFICATION D TO MODIFICATION A OF DOXAZOSIN MESYLATE

(75) Inventors: Peter Klein, Birkenheide; Marco Thyes, Ludwigshafen; Dieter Hix, Grosskarlbach, all of (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,778

(22) PCT Filed: Dec. 18, 1998

(86) PCT No.: PCT/EP98/08360

§ 371 (c)(1),
(2), (4) Date: Jul. 3, 2000

(87) PCT Pub. No.: WO99/35143

PCT Pub. Date: Jul. 15, 1995

(30) Foreign Application Priority Data

Jan. 6, 1998 (DE) .......................................... 198 00 214

(51) Int. Cl.[7] .................... A61K 31/497; C07D 239/72; C07D 403/00
(52) U.S. Cl. ................... 514/252.17; 544/291; 544/359
(58) Field of Search ..................... 514/252.17; 544/291, 544/359

(56) References Cited

U.S. PATENT DOCUMENTS 4,188,390 A    2/1980   Campbell .................... 424/251
6,130,218 A  * 10/2000  Morsdorf et al. ........... 514/253

FOREIGN PATENT DOCUMENTS

| | | |
|---|---|---|
| CA | 2224884 | 6/1998 |
| CA | 2224916 | 6/1998 |
| CA | 2225022 | 6/1998 |
| EP | 459 666 | 12/1991 |
| EP | 848 001 | 6/1998 |
| EP | 849 264 | 6/1998 |
| EP | 849 265 | 6/1998 |
| EP | 849 266 | 6/1998 |
| WO | 94/09783 | 5/1994 |
| WO | 96/39406 | 12/1996 |

OTHER PUBLICATIONS

XP002058927, Grcman et al., 292–293, Farm. Vest., 1997.
Chinese J.ofMed.Chem. vol. 5, No. 4, p 266, (1995).
XP002091815, Thermo. Acta 248 (1995), 1–59.
XP002101808,Threlfall, Analyst, 10/95,vol. 120,2435–2460, 1995.

* cited by examiner

Primary Examiner—Mukund J. Shah
Assistant Examiner—Tamthom N. Truong
(74) Attorney, Agent, or Firm—Keil & Weinkauf

(57) ABSTRACT

A process for preparing doxazosin mesylate in modification A which comprises dissolving doxazosin with methanesulfonic acid in methanol or a mixture of an aprotic, polar organic solvent and methanol, removing any turbidity from the resulting solution, and stirring the resulting clear solution until no further precipitate separates out, removing, washing with methanol, heating the precipitate in the moist state in ethanol and, after cooling, isolating the resulting product is described.

9 Claims, 6 Drawing Sheets

CONVERSION OF MODIFICATION D TO MODIFICATION A OF DOXAZOSIN MESYLATE

The present invention relates to a process for preparing doxazosin mesylate in a crystal modification referred to as form A, and to an intermediate through which this process proceeds.

Doxazosin (=4-amino-2-[4-(1,4-benzodioxane-2-carbonyl)piperazin-1-yl]-6,7-dimethoxyquinazoline) is a known substance (Merck Index, 12th Edition, 1996, No. 3489) which lowers blood pressure. The substance is mainly used in the form of the monomesylate which, in crystalline form, according to the statements in the Chinese Journal of Medicinal Chemistry 5(4), 266–270 (1995), at present occurs in 3 crystal modifications. The various modifications are referred to as modifications A, B and C in said citation. Modification A is obtained on recrystallization of doxazosin mesylate from ethanol. Modifications B and C result on recrystallization of doxazosin mesylate from chloroform and water respectively. Mention may be made of the fact that the Chinese Journal of Medicinal Chemistry in fact speaks only of doxazosin. However, according to the published data, the material must be doxazosin mesylate.

Although doxazosin is mostly used as monomesylate, the preparation of this salt has not to date been described. Concerning the known modifications of doxazosin mesylate, it has emerged that the mesylate does not dissolve even in 75 times the amount of chloroform at the boiling point. The product isolated after cooling the suspension contains chloroform, which is a solvent which is objectionable from the toxicological viewpoint and which can be removed only with difficulty and not without adverse effects on the active ingredient. Although the mesylate dissolves better in water, the product which results on cooling this solution can be isolated only with difficulty. In addition, the yield is poor and the material proves to be X-ray amorphous. The mesylate does not dissolve even in 350 times the amount of ethanol at the boiling point of the solvent. Hot filtration of the suspension affords a small yield of the described ethanol modification A as residue on the filter. Cooling the filtrate results in only a moderate yield of impure A modification.

Thus, not only has the preparation of doxazosin mesylate not to date been described, there is also no method which can be used on the industrial scale to obtain a particular modification of doxazosin mesylate. Of the described modifications, because of the properties indicated above, modifications B and C are unsuitable for developing a process. Only modification A is suitable for this on the basis of its properties.

A process which can be used on the industrial scale to prepare doxazosin mesylate in crystal modification A has now been found.

The present invention relates to a process for preparing doxazosin mesylate in modification A which comprises dissolving doxazosin with methanesulfonic acid in methanol, removing any turbidity from the resulting solution, and stirring the resulting clear solution until no further precipitate separates out, removing, washing with methanol, heating the precipitate in the moist state in ethanol and, after cooling, isolating the resulting product.

For the reaction of doxazosin with methanesulfonic acid, the two substances are employed in the molar ratio of about 1:1. A small molar excess of the sulfonic acid is preferably used (up to about 10%).

If the time between obtaining a solution by adding methanesulfonic acid to doxazosin and the appearance of a precipitate is insufficient for a filtration—for example if the reaction is to be carried out on the industrial scale—the time for the filtration can be extended by adding an aprotic, polar organic solvent to the methanol used for the reaction.

Examples of suitable aprotic, polar organic solvents in this case are N,N-dimethylformamide and, in particular, N-methyl-2-pyrrolidone. The ratio of doxazosin to methanol (weight/volume) or the ratio of doxazosin to methanol to the aprotic, polar organic solvent (weight/volume/volume) is about 1:(5 to 15), preferably about 1:(8 to 12) or about 1:(5 to 15):(1.5 to 4), preferably about 1:(8 to 12):(2 to 3).

If in the novel process any foreign particles present in the solution obtained after adding methanesulfonic acid are to be removed by filtration it is preferable to use a solvent mixture of aprotic, polar organic solvent and methanol in the first reaction stage. The reason is that in this case, as already mentioned, the time between obtaining the solution and the first crystal formation is greater than on use of methanol alone as solvent. If filtration of the solution obtained after adding methanesulfonic acid is desired in the first reaction stage of the novel process, a particularly preferred procedure is to use the solvent mixture with aprotic, polar organic solvent and moreover to add part of the methanol only after the filtration.

The precipitate resulting after the mixing of doxazosin and methanesulfonic acid represents a novel modification of doxazosin mesylate, which is referred to as modification D herein. The present invention likewise relates to this modification. It is characterized in particular by principal lines in the Debye-Scherrer X-ray diffractogram at the following values of 2 theta which are indicated in degrees of angle: $5.72 \pm 0.2°$, $11.10 \pm 0.2°$, $11.46 \pm 0.2°$, $14.14 \pm 0.2°$, $17.01 \pm 0.2°$, $17.78 \pm 0.2°$, $18.33 \pm 0.2°$, $20.73 \pm 0.2°$, $21.70 \pm 0.2°$, $23.12 \pm 0.2°$, $24.28 \pm 0.2°$, $26.58 \pm 0.2°$.

After its removal, doxazosin mesylate (modification D) is washed with methanol, and the product moist with solvent (moisture content about 10–60%, preferably 25–50%) is further processed to modification A of doxazosin mesylate.

Conversion of moist modification D takes place in a simple manner by heating in ethanol. This preferably entails heating under reflux. The amount of ethanol used should be such that a suspension is always present during the conversion. It preferably amounts to about ten times the amount of moist modification D employed, based on its dry weight, i.e. 100 ml of ethanol are used for 10 g of dry substance.

The novel process affords doxazosin mesylate in modification A in an overall yield of more than 85%. The purity of the modification A obtained by the novel process is excellent. Another considerable advantage of the novel process is that a solution is produced after addition of the methanesulfonic acid to the doxazosin. This makes it possible to remove any foreign particles present by filtration.

EXAMPLE 1

Preparation of Doxazosin Mesylate in Crystal Modification D

Process 1

14.1 g of anhydrous methanesulfonic acid were added to a stirred mixture of 63.2 g of doxazosin, 125 ml of N-methyl-2-pyrrolidone and 500 ml of methanol in a 1 l three-neck round-bottom flask. The internal temperature rose to 30° C. during this, and a solution was produced. After the addition of methanesulfonic acid was complete, the reaction mixture was filtered into a second 1 l three-neck round-bottom flask. The filter was washed with 85 ml of methanol, and the combined filtrates were stirred for 5 h. After the end of the stirring time, the resulting precipitate was filtered off with suction and washed 3× with 25 ml of methanol each time. 125 g of moist doxazosin mesylate (modification D) were obtained. This corresponds to 70.4 g of dry substance and a yield of 91.8%.

BRIEF DESCRIPTION OF DRAWINGS

Modification D of doxazosin mesylate was characterized by the Debye-Scherrer X-ray diffractogram, by the differential scanning thermogramm and by the IR spectrum (cf.

Process 2

Figure 1:
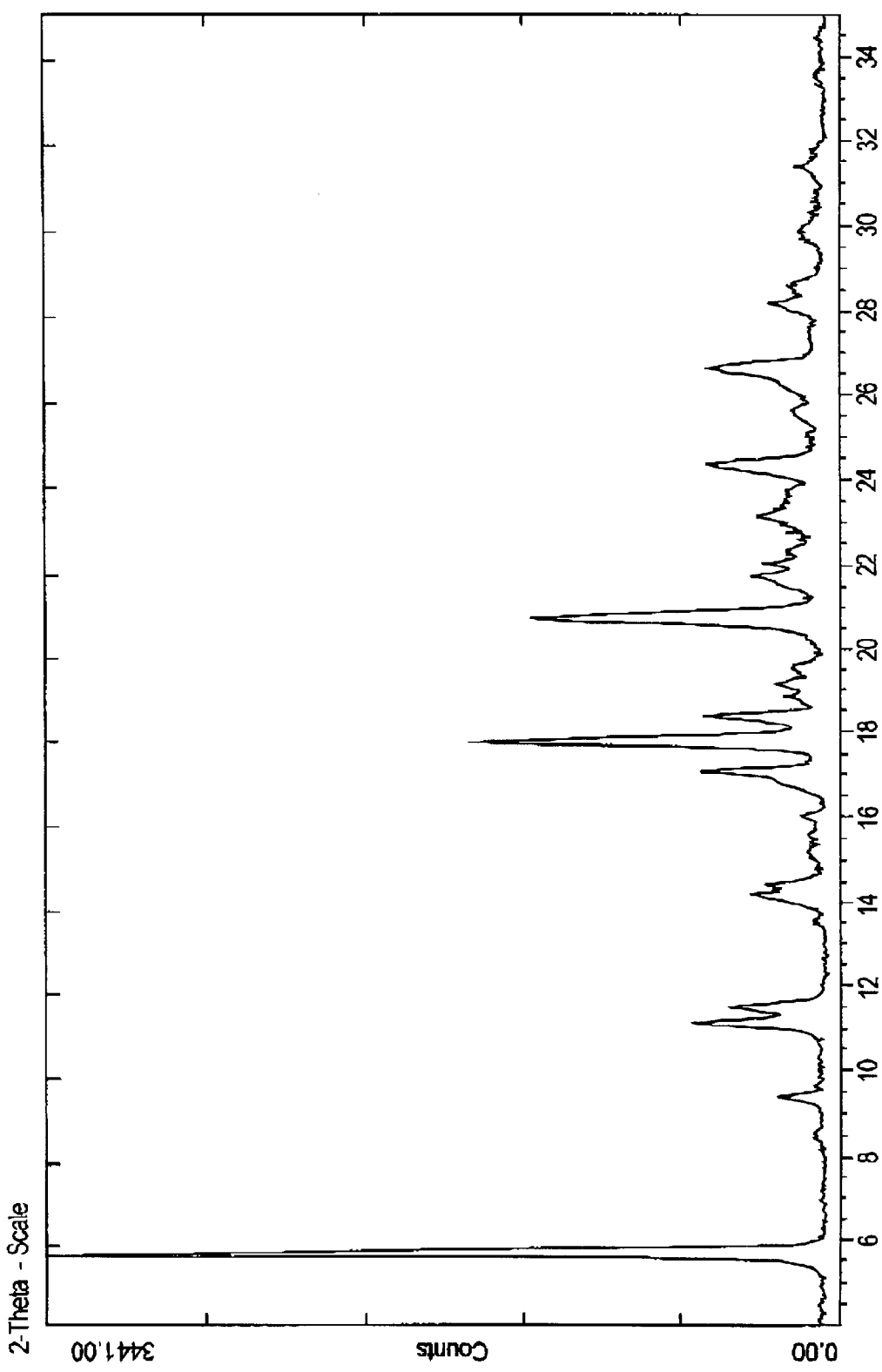
FIGS. 1–3; for the 2 theta values of the principal lines in the diffractogram, see above). All the data were obtained on vacuum-dried material. For the Debye-Scherrer X-ray diffractogram, the differential scanning thermogrammm and the IR spectrum of form A of doxazosin mesylate, see FIGS. 4–6.
Figure 2:
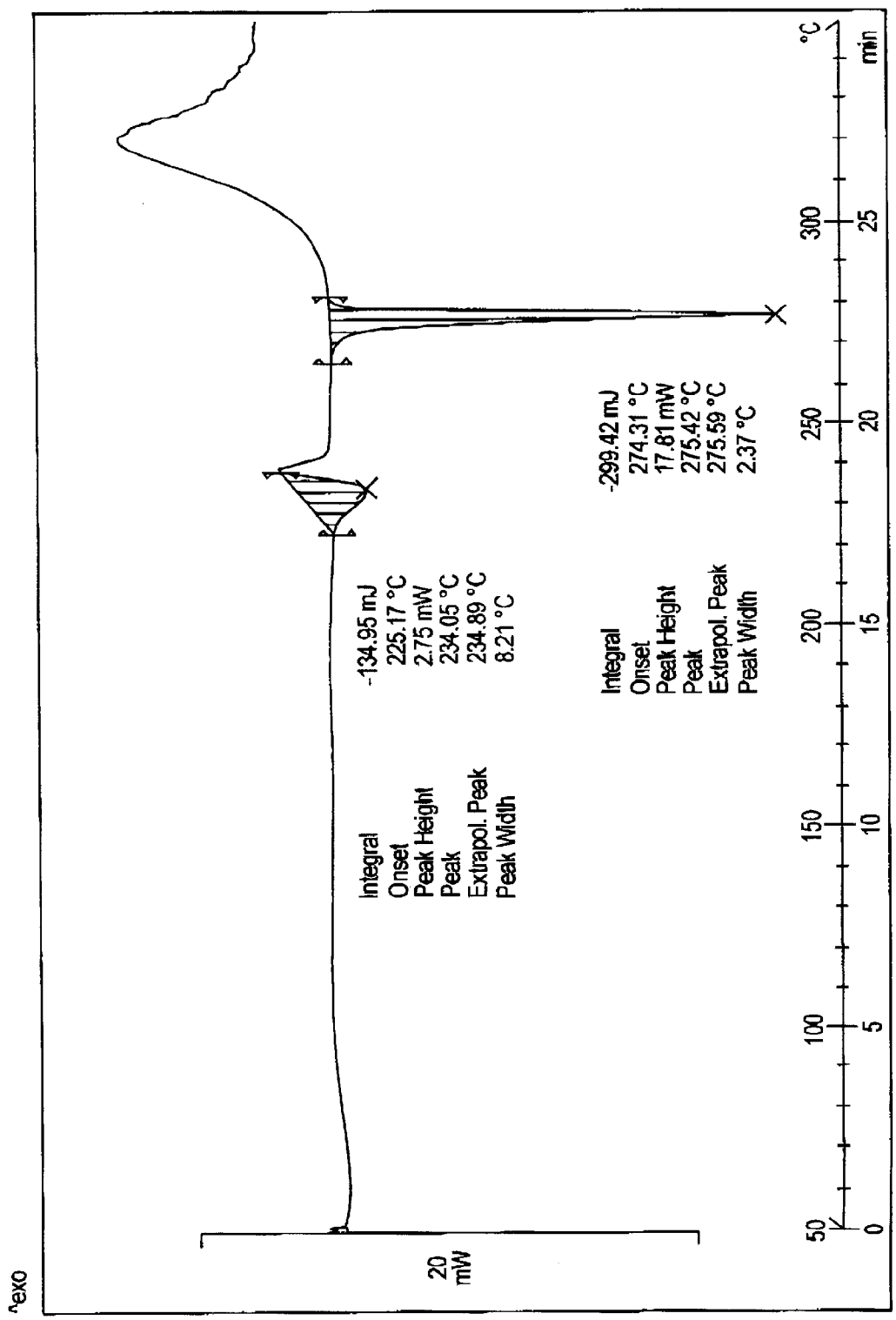
Figure 3:
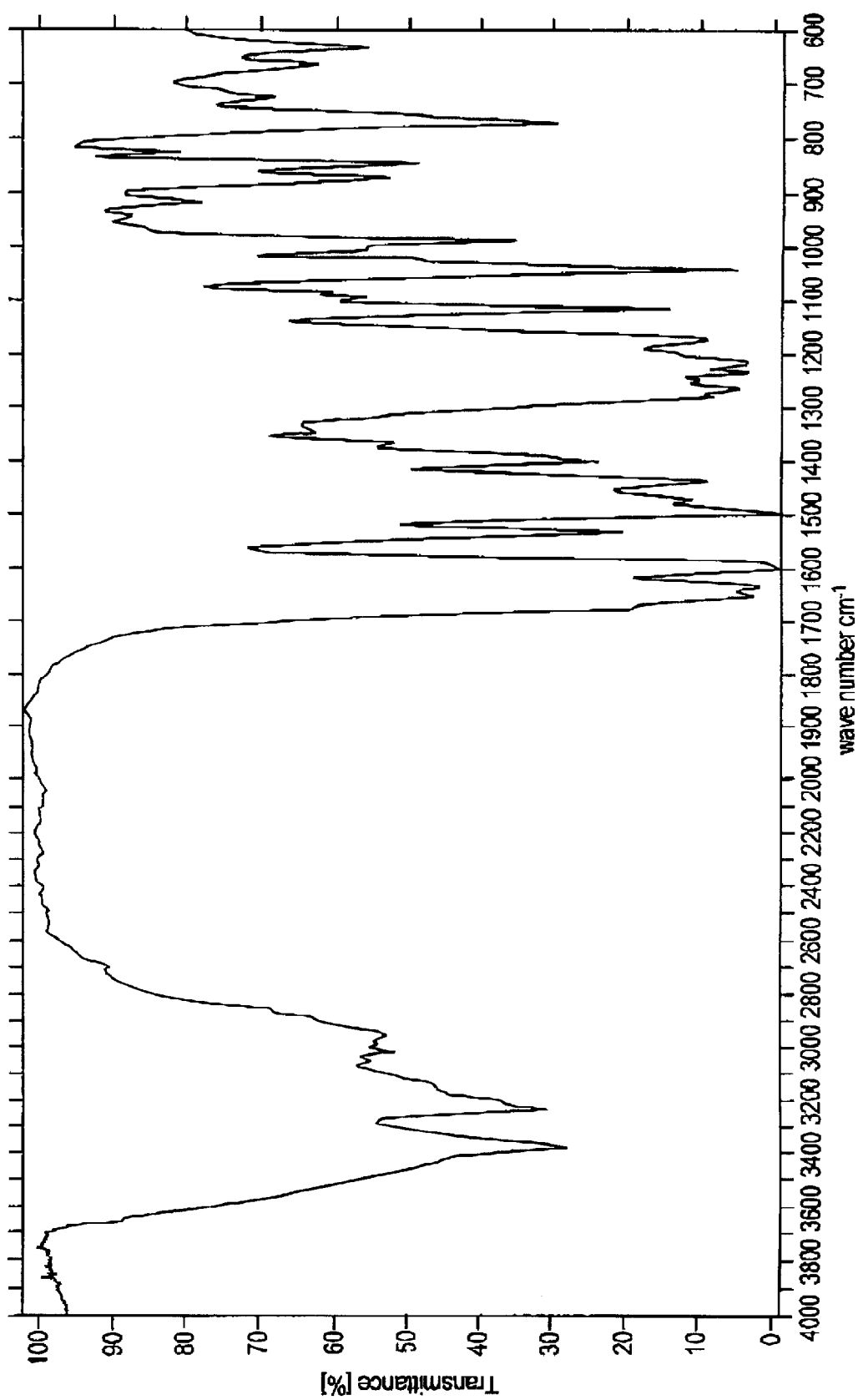
Figure 4:
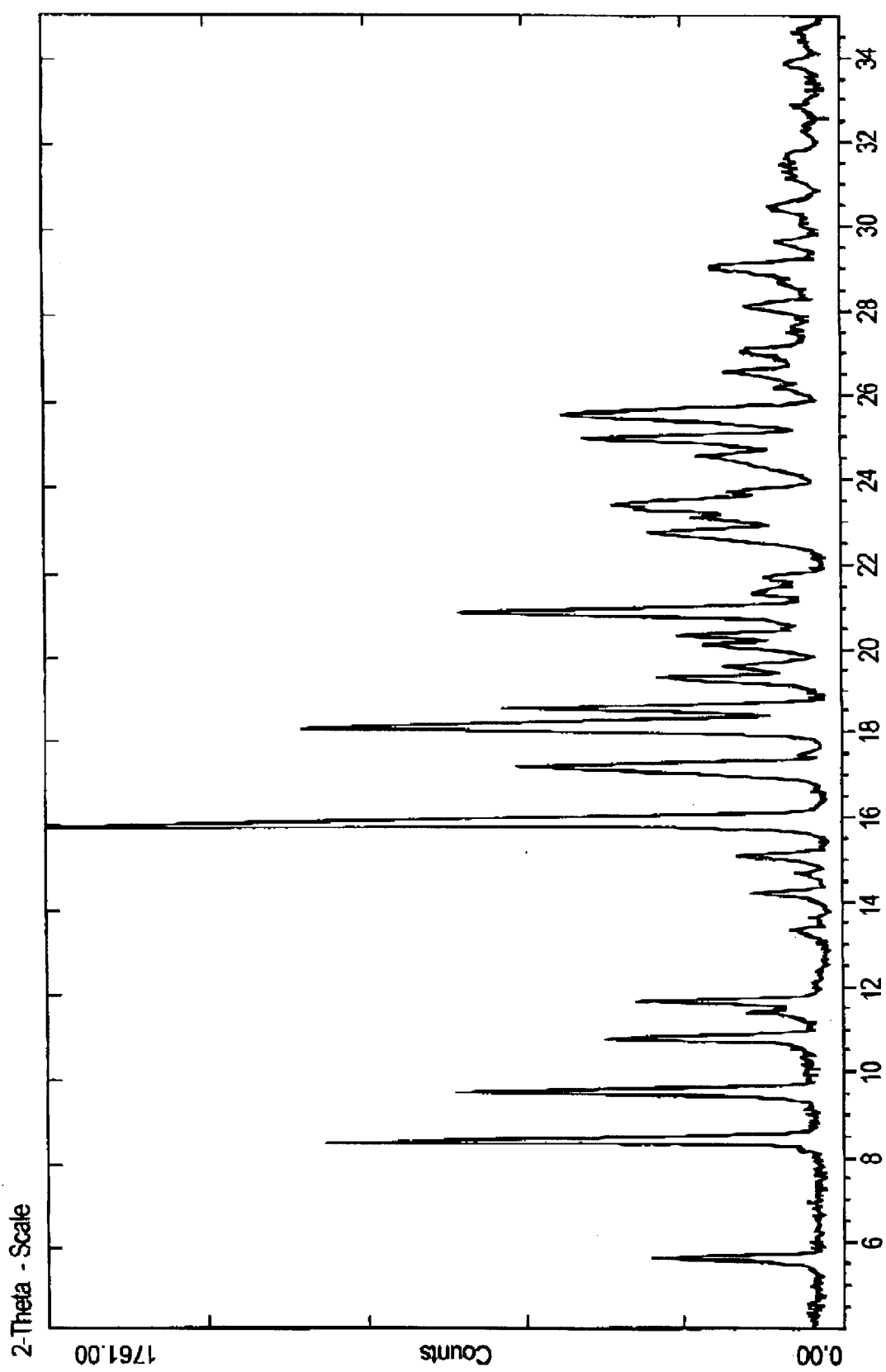
Figure 5:
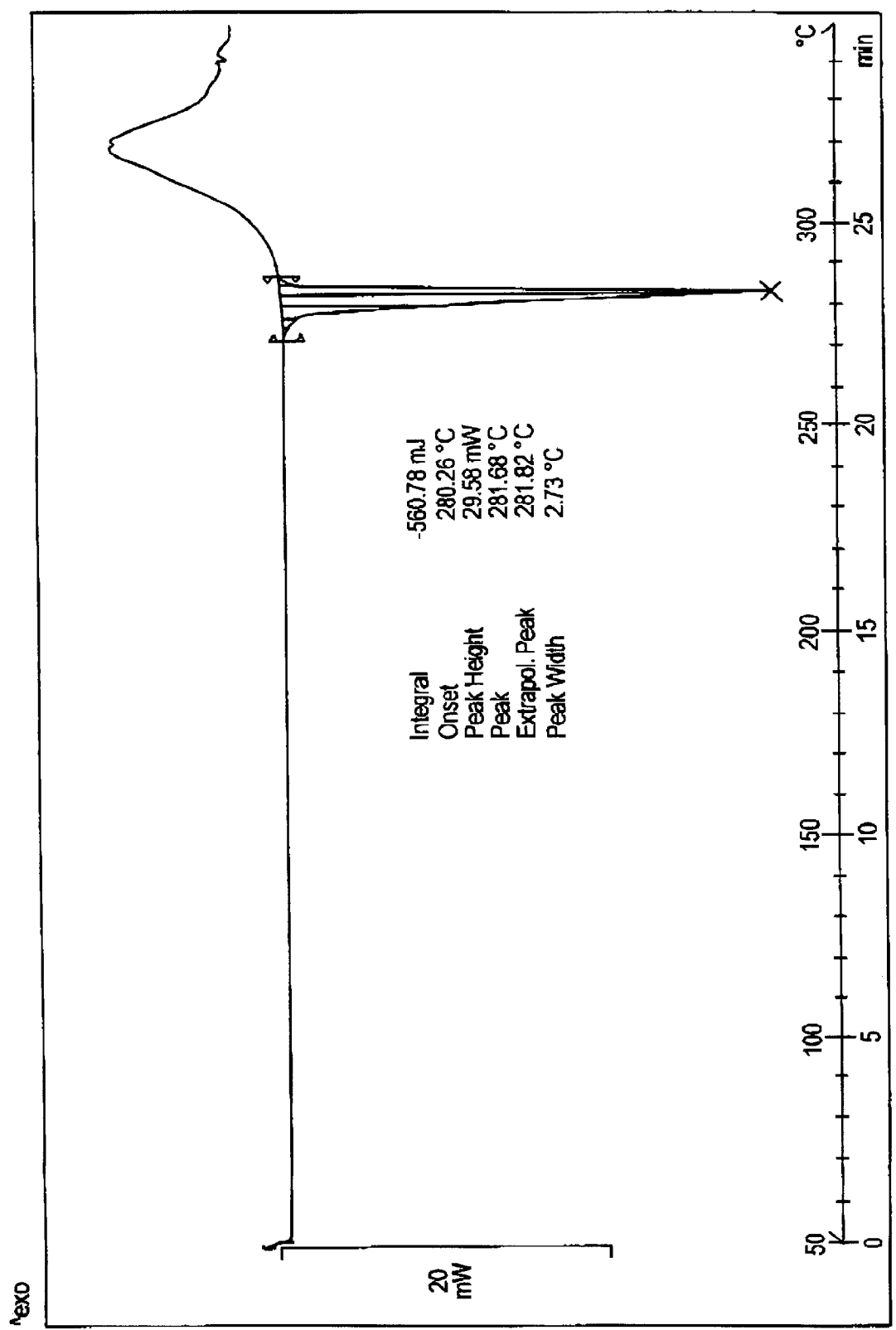
Figure 6:
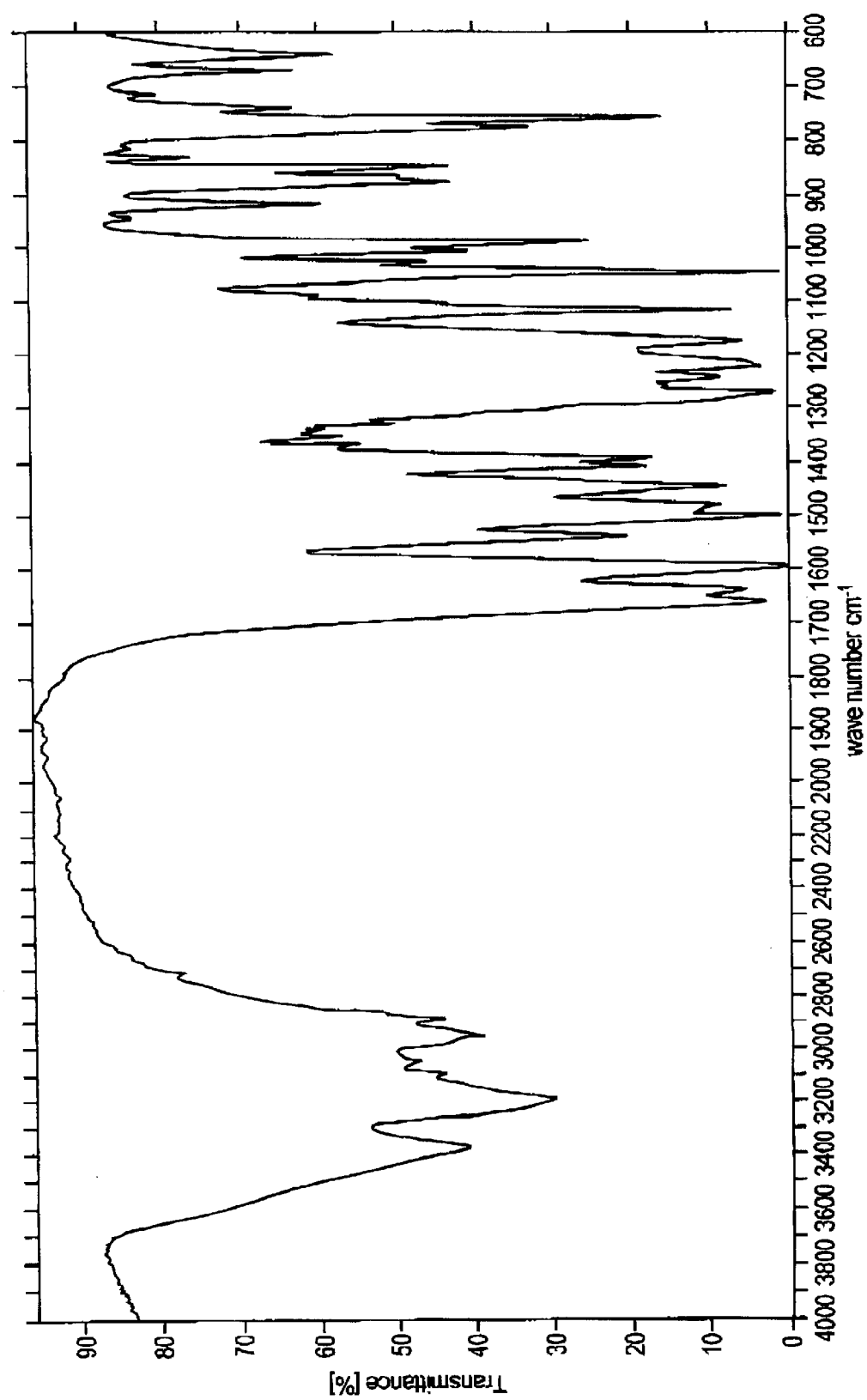

6.1 g of anhydrous methanesulfonic acid were added to a stirred mixture of 27.1 g of doxazosin, 54 ml of N-methyl-2-pyrrolidone and 250 ml of methanol in a 500 ml three-neck round-bottom flask. The internal temperature rose to 30° C. during this, and a solution was produced. After the addition of methanesulfonic acid was complete, the reaction mixture was filtered into a second 500 ml three-neck round-bottom flask, and the filtrate was stirred for 5 h. After the end of the stirring time, the resulting precipitate was filtered off with suction and washed 2× with 50 ml of methanol each time. 45 g of moist doxazosin mesylate (modification D) were obtained. This corresponds to 28.5 g of dry substance and a yield of 86.7%.

Process 3

17.7 g of anhydrous methanesulfonic acid were added to a stirred mixture of 79.0 g of doxazosin and 800 ml of methanol in a 2 l three-neck round-bottom flask. The internal temperature rose to 30° C. during this, and a solution was produced. After the addition of methanesulfonic acid was complete, the mixture was stirred for 5 h. The resulting precipitate was then.filtered off with suction and washed 3× with 50 ml of methanol each time. 141.8 g of moist doxazosin mesylate (modification D) were obtained. This corresponds to 89.2 g of dry substance and a yield of 93.1%.

EXAMPLE 2

Conversion of Moist Modification D of Doxazosin Mesylate into Modification A 120 g of the moist product obtained in Example 1, process 1 were taken up in 700 ml of ethanol in a 1 l three-neck round-bottom flask. The mixture was kept at the reflux temperature with stirring for 3 h (a solution at all times) and then cooled to room temperature. The undissolved solid was filtered off with suction, washed 2× with 25 ml of ethanol each time, and dried in vacuo at 75° C. 63.9 g of doxazosin mesylate were obtained in form A. This corresponds to a yield of 94.2% based on the amount of modification D employed.

We claim:

1. Doxazosin mesylate which is characterized by exhibiting two melting peaks in a differential scanning thermogramm, where the first melting peak has an onset at 225.17° C. and the second melting peak has an onset at 274.31° C., and which is designated as modification D.

2. Doxazosin mesylate which is characterized by principal lines in Debye-Scherrer X-ray diffractometry at the following values 2Θ (indicated in degrees of angle): 5.72±0.2°, 11.10±0.2°, 11.46±0.2°, 14.14±0.2°, 17.01±0.2°, 17.78±0.2°, 18.33±0.2°, 20.73±0.2°, 21.70±0.2°, 23.12±0.2°, 24.28±0.2°, and 26.58±0.2°, and which is designated as modification D.

3. A process for preparing doxazosin mesylate in modification A which comprises first preparing doxazosin mesylate having a modification D as defined in claim 1 by i) dissolving doxazosin with methylsulfonic acid in methanol or in a mixture of methanol and an aprotic, polar organic solvent, ii) removing any residual turbidity from the methanol solution, iii) stirring the methanol solution to obtain a precipitate of doxazosin mesylate having the modification D, iv) separating the precipitate from the methanol phase, and v) washing the separated precipitate with methanol, and subsequently converting the modification D into the modification A by vi) heating the washed precipitate in the moist state in ethanol, and, vii) after cooling, isolating the resulting modification A.

4. The process of claim 3, wherein the mixture of an aprotic, polar organic solvent and methanol is used in reaction stage (i).

5. The process of claim 3, wherein the mixture of an aprotic, polar organic solvent and methanol is used in reaction stage (i), and additional methanol is added after stage (ii) and prior to stage (iii).

6. The process of claim 3, wherein the washed precipitate utilized in stage (vi) has a moisture content of from 10 to 60%.

7. The process of claim 3, wherein the washed precipitate utilized in stage (vi) has a moisture content of from 25 to 50%.

8. The process of claim 3, wherein doxazosin and methylsulfonic acid are employed in a molar ratio of about 1:1.

9. The process of claim 3 wherein methylsulfonic acid is employed in a molar excess, based on the amount of doxazosin, of up to 10%.

* * * * *